(12) United States Patent
Budman et al.

(10) Patent No.: US 6,576,013 B1
(45) Date of Patent: Jun. 10, 2003

(54) EYE PROSTHESIS

(75) Inventors: Mark Budman, Vestal, NY (US); James R. Stack, Endicott, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/041,342

(22) Filed: Jan. 8, 2002

(51) Int. Cl.$^7$ .................................................. A61F 2/14
(52) U.S. Cl. ...................................... 623/6.64; 446/392
(58) Field of Search ................................ 623/4.1, 6.64, 623/FOR 103; 434/271; 446/392

(56) References Cited

U.S. PATENT DOCUMENTS

| | | |
|---|---|---|
| 3,364,501 A | 1/1968 | Stafford |
| 3,480,971 A | 12/1969 | Smith |
| 4,272,910 A | 6/1981 | Danz |
| 4,305,223 A * | 12/1981 | Ho .............................. 446/392 |
| 5,026,392 A | 6/1991 | Gordon |
| 5,108,427 A | 4/1992 | Majercik et al. |
| 5,171,265 A | 12/1992 | Kelley |
| 5,326,346 A | 7/1994 | Cortes |
| 6,139,577 A | 10/2000 | Schleipman et al. |
| 6,391,057 B1 * | 5/2002 | Schleipman et al. ....... 623/6.64 |

FOREIGN PATENT DOCUMENTS

| | | |
|---|---|---|
| AU | WO8601996 A1 | 4/1986 |
| DE | 19850807 A1 | 5/2000 |
| GB | 2055584 A | 3/2000 |

OTHER PUBLICATIONS

Derwent abstract of ZA 9205915 (South African patent document published Aug. 6, 1992).

* cited by examiner

Primary Examiner—David H. Willse
(74) Attorney, Agent, or Firm—John R. Pivnichny

(57) ABSTRACT

An ocular prosthesis displays an iris and pupil image on a color liquid crystal array display device. A plurality of iris images are stored as data in a memory. Ambient light level is detected by a light sensor device. An image is selected based on light level and sent to the array display device.

20 Claims, 2 Drawing Sheets

EYE PROSTHESIS

TECHNICAL FIELD

The invention relates to ocular prosthetic devices in general. More particularly the invention relates to an ocular prosthesis having means for adjusting the apparent pupil size or iris dilation in response to ambient light levels and a method for accomplishing same.

BACKGROUND OF THE INVENTION

Eye prosthesis devices simulate the appearance of a natural eye and therefore provide a better facial appearance to someone who has lost one or both eyes. In the past a spherical or globe shaped device having an eye image on the surface was inserted in the vacant socket from which the natural eye was removed.

A much better appearance is provided, however if the artificial eye moves in tandem with a natural eye. Various methods have therefore been developed for attaching the eye movement muscle tendons to a ball shaped eye socket insert. The ball will then move in tandem with a natural eye through a well known process of sympathetic muscle action.

For example, Stafford in U.S. Pat. No. 3,364,501 describes an inflatable eye prosthesis to which six eye movement muscles are attached. Gordon in U.S. Pat. No. 5,026,392 describes a ball shaped prosthetic eye having tabs for attaching to four eye muscles. The tabs with the attached eye muscles are inserted into receiving regions on the spherical prosthetic eye. The tabs may be adjusted by removing and re-inserting into the receiving region and thereby position the eye to rest in a natural orientation with respect to the natural eye.

While an eye image may be placed on the ball itself, it is advantageous to provide a front section which is easily removable, and place the eye image on this front section. This two part construction permits the front section to be easily replaced as required. In one arrangement, the front section is substantially hemispherical so that when the prosthesis is inserted the front surface rests against the inner surface of the eyelids permitting normal opening and closing of the eyelids. The back surface rests on the ball inserted in the eye socket. A peg protruding from the ball may rest in a depression in the back surface of the front section and serve to transfer movement of the ball to the front section. Currently used materials such as light-cured urethane dimethacrylate of U.S. Pat. No. 5,326,346 or TRIAD II light cured acrylic resin supplied by Dentsply of York, Pa. of U.S. Pat. No. 5,171,265 or other acrylics are eventually attacked by body fluids in the lid area, tears etc., causing the image to deteriorate. Replacement at about five year intervals is therefore required. Removal of the front section also permits cleaning and re-insertion on a frequent basis. The difficulty of removing a front section is therefore comparable to removal of a contact lens.

Typically, a sclera, iris, and pupil matching the natural eye are painted on the ball or removable front section during manufacture by a professional person known as an ocularist. However, once painting is complete, the size of the pupil is fixed on the artificial eye. The natural eye will have a changing pupil size depending on ambient light as is well known. The ocularist therefore selects an intermediate size for the painted pupil as a best match.

Various devices and methods have been developed to provide adjustment of the pupil size in a prosthetic eye, however none are currently in wide use. Smith, in U.S. Pat. No. 3,480,971 describes a mechanical dilator which is responsive to muscle movement in the eye socket to provide control over pupil size. Danz, in U.S. Pat. No. 4,272,910 describes a fixed iris image within the body of an artificial eye. The image has a central dark portion simulating a pupil in a bright light condition. An annular ring of electro-optically sensitive material such as liquid crystal display (LCD) material is placed in front of the iris and concentrically surrounding the pupil simulating central dark portion. The outer diameter of the ring is selected to simulate the diameter of a pupil in a less than bright environment. The annular ring is normally transparent. When a photoelectric sensor detects a light level below a fixed threshold, a voltage source and switch excite the annular ring to make the pupil appear to dilate e.g. the ring becomes opaque black. Trefry and Saul in PCT application WO86/01996 describe a similar apparatus having several concentric rings which are activated in sequence as the ambient light diminishes thus simulating the pupil dilating in several steps. Boshoff, in the abstract of South Africa patent ZA 9205915 also describes a number of concentric rings of liquid crystal material activated in response to a photodiode. Majercik et al. in U.S. Pat. No. 5,108,427 also describes a series of concentric rings of a photochromic material requiring no electrical or mechanical excitation, but merely chemical reaction to incident light e.g. turning from transparent to opaque.

Schleipman et al. in U.S. Pat. No. 6,139,577 also use a series of concentric rings of LCD material to simulate a range of dilation and contraction of a pupil. In their device, however, a special pixelated iris image is created from a digital photograph of a desired natural iris by removing a number of pixels to provide clear non-image areas. The pixelated photograph is then color adjusted before printing so that it has a color and pattern approximating the natural eye when viewed in front of a liquid crystal display through the pixels. As concentric rings of the LCD are selectively activated and darkened, the portions of the pixelated iris with the activated LDC behind will appear as a pupil of various degrees of dilation.

Volker in the abstract of German patent DE 19850807A1 describes an artificial iris using overlapped color filters and a phototropic material which changes color to simulate contraction of a pupil in a bright light.

As noted above, none of these developments are in widespread use today. In accordance with the teachings of the present invention there is presented a new apparatus and method for adjusting pupil size in an ocular prosthesis. It is believed that such a device constitutes a significant advancement in the art.

Even though eye prosthesis are primarily intended for human use, it will be obvious to those of skill in the art that application will also extend to use in animals, dolls, mannequins, robots or any other objects having an eye.

OBJECTS AND SUMMARY OF THE INVENTION

It is therefore a principal object of the present invention to enhance the ocular prosthetic art by providing a device with enhanced capability.

It is another object to provide such a device which can be economically produced and widely used.

It is yet another object to provide a novel method of adjusting pupil size in an eye prosthesis.

These and other objects are attained in accordance with one embodiment of the invention wherein there is provided an adjustable iris image for an artificial eye, comprising, a color liquid crystal display positioned within the artificial eye, a memory chip coupled to the color liquid crystal display having a plurality of patterns corresponding to a plurality of iris images to be shown on the color liquid crystal display, a light sensor coupled to the memory, and means for sending in response to the light sensor, one of the plurality of patterns to the color liquid crystal display.

In accordance with another embodiment of the invention there is provided an eye prosthesis, comprising, a shell having a convex surface, a liquid crystal array display device positioned behind the convex surface and within the shell, memory means coupled to the display device having a plurality of data patterns corresponding to eye iris images with differing pupil sizes, for exhibiting on the display device, a light sensor coupled to the memory means, and a control circuit for selecting one of the plurality of data patterns in response to the light sensor and transferring the data pattern to the display device.

In yet another embodiment of the invention there is provided a method of adjusting pupil size in an eye prosthesis, comprising the steps of, providing an eye prosthesis having a substantially circular array of color liquid crystal display elements, a memory device, and a light sensing device, storing a plurality of data patterns in the memory device, the data patterns corresponding to eye iris images with differing degrees of pupil size, and sensing a level of ambient light with the light sensing device and therefrom selecting one of the plurality of data patterns in the memory device and displaying the corresponding eye iris image on the array of color liquid crystal display elements.

BEST MODE FOR CARRYING OUT THE INVENTION

For a better understanding of the present invention, together with other and further objects, advantages and capabilities thereof, reference is made to the following disclosure and the appended claims in connection with the above-described drawings.

Figure 1:
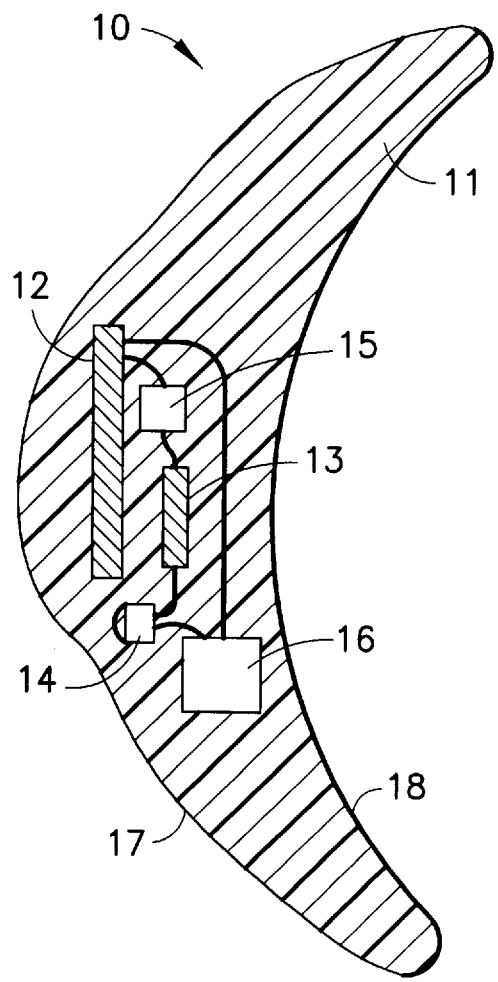
FIG. 1 is a cross sectional view of an ocular prosthesis.

In FIG. 1 there is shown in cross section an eye prosthesis 10. A shell 11 is appropriately shaped having a convex front surface 17. Back surface 18 may be concave to rest on a ball within an eye socket while the extremities of front surface 17 fit behind the lids. A depression (not shown) may be included on back surface 18 to accommodate a corresponding peg in the ball for effectively transferring ball motion to prosthesis 10 as explained above. In complementary fashion, a peg (not shown) may extend from back surface 18 to fit in a depression in the ball for the same purpose. Shell 11 may be constructed from a white acrylic solid material such as light-cured acrylic resin or urethane dimethacrylate.

Interior to shell 11 is a color liquid crystal display 12 positioned to simulate a natural iris. Display 12 may have a substantially circular periphery. Display 12 has an array of pixel elements sufficiently small to accurately show a color image of a natural iris including a dark centered pupil. Shell 11 is necessarily transparent in front of display 12.

The actual iris image or pattern shown at any particular time is stored in memory 13 also located interior to shell 11. Memory 13 may be any type of memory including a memory chip such as a dynamic or static random access memory (DRAM or SRAM). Preferably memory 13 is a nonvolatile memory such as a programmable memory (PROM), electronically programmable memory (EPROM), electronically erasable programmable memory (EPROM), or flash memory.

A plurality of patterns corresponding to a plurality of iris images are stored as data in memory 13. For example, one iris image may represent a natural iris in a bright ambient light condition having a relatively small pupil diameter. A second image may represent the same iris in a low ambient light condition and therefore appear dilated, having a large pupil diameter. Additional iris images having other pupil diameters may also be stored in memory 13.

Light sensor 14, also located within shell 11, is coupled to memory 13. Light sensor 14 detects the ambient light level. It is necessary that shell 11 be at least partially transparent to ambient light in front of light sensor 14. However, the coloring of shell 11 is selected to simulate the natural eye color (white) and render light sensor 14 invisible.

In response to light sensor 14, data representing one of the plurality of images or patterns stored in memory 13 is sent to the color array liquid crystal display 12. A control circuit 15 or other means such as a microprocessor may be used to send image data from memory 13 to display 12. Any method of sending data may be used including use of a serial or parallel data bus. Control circuit 15 may be positioned on, or integrated on the same chip as memory 13.

A power source 16 may be provided for operating display device 12. For example, a small replaceable mercury battery located within shell 11 may be used. Other types of primary and rechargeable batteries may also be used. Additional power may be provided by a solar device coupled to power source 16. Light sensor 14, itself maybe a solar device in which case it may provide a dual function of detecting ambient light level and providing electrical power. Other known means of providing power to prosthetic devices such as magnetic induction, radio frequency waves, and electrical contacts may also be used without departing from the scope of the invention.

All of the devices within shell 11 may be positioned within a hollow cavity interior to shell 11. Various methods are known for constructing a hollow prosthesis are known, for example see U.S. Pat. No. 5,171,265 which is incorporated herein by reference. The devices may also be completely encapsulated by the shell material so that no cavity is needed.

Instead of a plurality of iris images having differing pupil sizes, other images may also be stored in memory 13. For example, both blue and brown, or other colors of iris images may be stored. In fact any image may be stored in memory 13. Various methods may be used to re-program memory 13 including but not limited to providing one or more electrical contacts (not shown) on a surface of prosthesis 10. Such contacts if provided may also be used to re-charge power source 16.

Figure 2:
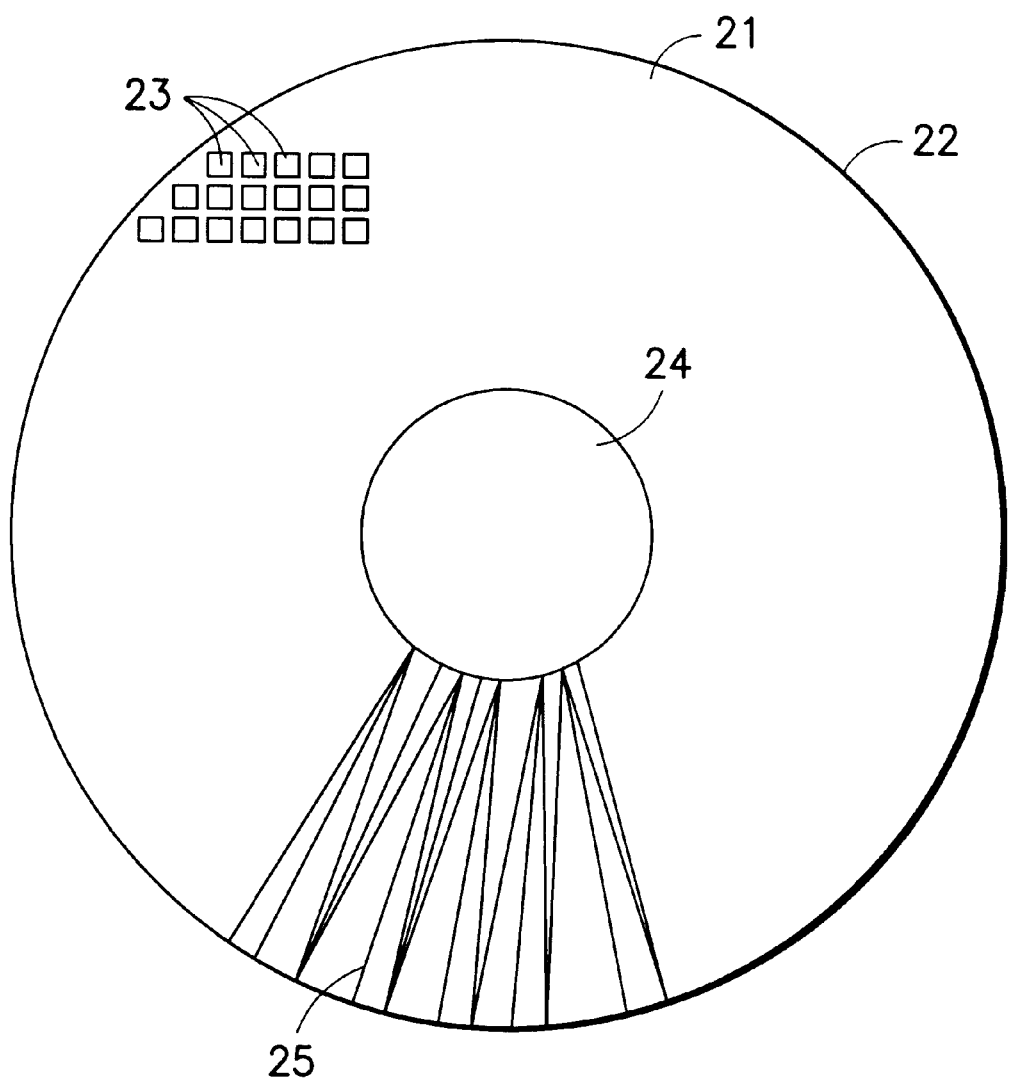
FIG. 2 is a front view of a LCD display device as used in the present invention.

In FIG. 2 there is shown a partial front view of an array LCD display having a substantially circular perimeter 22. An array of LCD pixel elements 23 completely covers the interior 21 of periphery 22 although a small portion are shown in FIG. 2. When activated by a pattern sent from memory 13, the pixels show an image of an iris, shown partially as 25, with a central dark pupil 24. The diameter of pupil 24 will depend on the data sent from memory 13.

Figure 3:
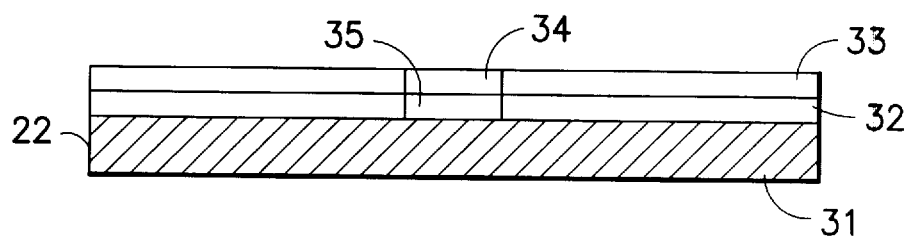
FIG. 3 is a cross section of a LCD display and other portions of another embodiment of the present invention.

Those skilled in the semiconductor arts will recognize that control circuit 15, memory 13, light sensor 14 and power source 16 can be all or partially constructed on a single semiconductor chip and that an LCD display may also be constructed on the chip so that various levels of electronic integration may be used in implementing the present invention. Shown in FIG. 3 is a cross section of one such integrated implementation. Semiconductor chip 22, has memory 13, control circuit 15, and power source 16 integrated in top layer 32 of a round silicon substrate 31. A combination light sensor/solar cell is integrated in a central area 35 having a diameter smaller than the smallest pupil size. An array of LCD devices is constructed in layer 33 atop layer 32. In the central area 34, no LCD pixels are present. Instead a non-reflective dark appearing covering which is at least partially transparent to ambient light is placed over light sensor 35. This integrated implementation is placed within an ocular prosthesis in the position shown for LCD 12 of FIG. 1. Other full or partial implementations may also be used without departing from the scope of the invention.

While there have been shown and described what are at present considered the preferred embodiments of the invention, it will be obvious to those skilled in the art that various changes and modifications may be made therein without departing from the scope of the invention as defined by the appended claims.

What is claimed is:

1. An adjustable iris image for an artificial eye, comprising;
   a color liquid crystal display positioned within said artificial eye;
   a memory chip coupled to said color liquid crystal display having a plurality of patterns corresponding to a plurality of iris images to be shown on said color liquid crystal display;
   a light sensor coupled to said memory chip; and
   means for sending in response to said light sensor, one of said plurality of patterns to said color liquid crystal display.

2. The iris image of claim 1, wherein said liquid crystal display, said memory chip, and said light sensor are all positioned on a single semiconductor substrate.

3. The iris image of claim 1, further comprising a power source coupled to said liquid crystal display.

4. The iris image of claim 3, wherein said power source comprises a solar device for converting ambient light into electrical power.

5. The iris image of claim 4, wherein said solar device is said light sensor.

6. The iris image of claim 1, wherein said sending means comprises a serial data bus.

7. The iris image of claim 1, wherein said sending means comprises a control circuit.

8. The iris image of claim 7, wherein said control circuit is positioned on said memory chip.

9. An eye prosthesis, comprising:
   a shell having a convex surface;
   a liquid crystal array display device positioned behind said convex surface and within said shell;
   memory means coupled to said display device having a plurality of data patterns corresponding to eye iris images with differing pupil sizes, for exhibiting on said display device;
   a light sensor coupled to said memory means; and
   a control circuit for selecting one of said plurality of data patterns in response to said light sensor and transferring said data pattern to said display device.

10. The eye prosthesis of claim 9, wherein said shell is a white acrylic solid.

11. The eye prosthesis of claim 9, wherein said liquid crystal array display device has a substantially circular periphery.

12. The eye prosthesis of claim 9, wherein said memory means comprises a semiconductor chip.

13. The eye prosthesis of claim 9, wherein said memory means is a nonvolatile memory.

14. The eye prosthesis of claim 9, wherein said memory means is a read only memory.

15. The eye prosthesis of claim 9, wherein said light sensor is positioned within said shell.

16. The eye prosthesis of claim 9, wherein said light sensor is electrically coupled to said control circuit.

17. A method of adjusting pupil size in an eye prosthesis, comprising the steps of:
    providing an eye prosthesis having a substantially circular array of color liquid crystal display elements, a memory device, and a light sensing device;
    storing a plurality of data patterns in said memory device, said data patterns corresponding to eye iris images with differing degrees of pupil size; and
    sensing a level of ambient light with said light sensing device and therefrom selecting one of said plurality of data patterns in said memory device and displaying said corresponding eye iris image on said array of color liquid crystal display elements.

18. The method of claim 17, further comprising the step of transferring said one of said plurality of data patterns from said memory device to said array of color liquid crystal display elements over a serial bus.

19. The method of claim 18, wherein said memory device is a semiconductor chip positioned within said eye prosthesis.

20. The method of claim 19, wherein said data patterns are stored in said memory device using said serial data bus.

* * * * *